United States Patent [19]
Geible

[11] Patent Number: 5,913,902
[45] Date of Patent: Jun. 22, 1999

[54] ARTIFICIAL FOOT THAT ENABLES LIMP-FREE WALKING

[76] Inventor: Harry F. Geible, 3428 Waterwood Dr., Sebring, Fla. 33872

[21] Appl. No.: 09/119,388

[22] Filed: Jul. 20, 1998

Related U.S. Application Data

[63] Continuation-in-part of application No. 08/965,459, Nov. 6, 1997, abandoned, which is a continuation-in-part of application No. 08/724,142, Sep. 30, 1996, abandoned.

[51] Int. Cl.$^6$ ........................................................ A61F 2/66
[52] U.S. Cl. ................................................. 623/55; 623/52
[58] Field of Search ........................................ 623/47–56

[56] References Cited

U.S. PATENT DOCUMENTS

| | | | |
|---|---|---|---|
| 16,360 | 1/1857 | Jerrett | 623/55 |
| 92,031 | 6/1869 | Foster | 623/55 |
| 409,311 | 8/1889 | Snyder | 623/55 |
| 804,207 | 11/1905 | Bunderle | 623/55 |
| 809,875 | 1/1906 | Wilkens | 623/55 |
| 1,215,268 | 2/1917 | Hagey | 623/55 |
| 2,430,584 | 11/1947 | Roche | 623/52 |

*Primary Examiner*—David H. Willse
*Assistant Examiner*—Bruce E. Snow
*Attorney, Agent, or Firm*—Ronald E. Smith

[57] ABSTRACT

An improved energy-storing artificial foot, connectable onto a lower end of an artificial leg worn by a leg amputee, includes a ball of foot part, a main foot part, and an ankle part. The artificial foot includes first and second transversely positioned pivotal axes that are spaced longitudinally from one another. The first axis, carried in the ankle part, is positioned in vertical alignment with a longitudinal axis of an artificial leg, is about four times higher from a ground surface than is the second axis, and is positioned 78% of the length of the artificial foot as measured from the forward end of the foot. The second axis is positioned in the ball of the foot region of the artificial foot, which is about a third of the length of the foot as measured from a forward end of the foot. A pair of vertically disposed compression springs flank the first axis to simulate muscles that support an ankle. A third compression spring, disposed at a predetermined angle relative to a support surface, and which is housed so that it extends between the main foot part and the ball of foot part, provides resistance to pivoting of the ball of foot part relative to the main body part of the artificial foot and otherwise serves as the arch of the foot. The positioning of the first and second axes relative to the forward end of the articial foot, relative to each other and relative to the support surface is critical, as is the positioning of the ball of foot spring, because such positioning of parts collectively enables a user to walk without limping and to climb or descend stairs without restriction. The foot automatically adjusts, requiring no shims, to shoes of differing heel heights.

2 Claims, 2 Drawing Sheets

ARTIFICIAL FOOT THAT ENABLES LIMP-FREE WALKING

CROSS-REFERENCE TO RELATED APPLICATIONS

This application is a continuation-in-part of a application bearing Ser. No. 08/965,459, filed Nov. 6, 1997, now abandoned entitled "Artificial Foot That Enables Limp-Free Walking" by the same inventor which is a continuation-in-part of 08/724,142, filed Sep. 30, 1996, now abandoned.

BACKGROUND OF THE INVENTION

1. Field of the Invention

This invention relates, generally, to the art of prosthetic devices. More particularly, it relates to an improved artificial foot worn by a leg amputee, including above and below knee amputees.

2. Description of the Prior Art

There are many patented prosthetic devices that are intended to perform the functions of the human foot. However, the devices known heretofore share a common trait: they cause the amputee to limp. Thus, none of the known prosthetic feet successfully replicate the flexure, feel, and steadiness of a natural foot.

The problem of creating an artificial foot that does not cause its wearer to limp is one of the most intractable problems in the field of prosthetics.

For example, U.S. Pat. No. 2,430,584 to Roche discloses an artificial foot having a joint that allows the toe part of the prosthesis to bend, thereby replicating at least to some degree the action of that important part of a foot. However, a human foot actually bends at the ball of the foot when walking, i.e., at a point rearwardly of the base of the toes. As a result, a person wearing an artificial foot of the type disclosed in said patent will have a noticeable limp. More particularly, the device does not bend where it should, with the result that the walker rises higher than normal when striding on the artificial foot; when a stride of the artificial foot is followed by a stride on the natural foot, the natural foot must catch the fall from the unnaturally high position attained by the leg of the walker associated with the artificial foot. The result is a clearly noticeable limp.

Additional patents in the field include U.S. Pat. Nos. 92,031 to Foster and 1,215,268 to Hagey.

All three of these earlier contributions to the art include a first hinge in the general area of the toe joints and a second hinge in the general area of the ankle of the artificial foot. If the total length of an artificial foot is defined as the distance from the tip of the toes to the back of the heel, and if the distance of the first (toes) and second (ankle) joints is described as a percentage of the distance from said tip of said toes to said back of said heel, the respective positions of the first and second joints of the three above-mentioned prior art contributions are as follows:

| Roche | Foster | Haney |
|---|---|---|
| 21%/66% | 30%/66% | 25%/75% |

Many patented artificial feet have been sold, and they have enabled many amputees to walk. However, if a design could be found that would eliminate the limp caused by the earlier designs, amputees would benefit.

Another shortcoming of the artificial feet heretofore known is that they require the placing of shims beneath the heel portion thereof to allow the user to wear differing types of shoes having differing heel heights. Thus, when a user switches from one type of shoes, such as tennis shoes, for example, to another type of shoes, such as cowboy boots, for example, the number of shims must be changed.

Accordingly, there is a need for an artificial foot that would automatically adjust, in the absence of shims, to changes in shoe heel heights.

However, in view of the art considered as a whole at the time the present invention was made, it was not obvious to those of ordinary skill in this art how the needed improvements could be provided.

SUMMARY OF THE INVENTION

The long-standing but heretofore unfulfilled need for an apparatus that overcomes the limitations of the prior art is now met by a new, useful, and nonobvious artificial foot that is connectable to the lower end of an artificial leg. The novel structure represents a significant, substantial improvement over the artificial feet heretofore known because it is the first artificial foot, anywhere in the world, that does not cause its wearer to limp. The structure very closely duplicates the action, response and feel of a natural foot.

More particularly, the invention includes a ball of foot part, a main foot part, and an ankle part. The ankle part is mounted on a first pivotal axis, is in vertical alignment with an artificial leg and is received within an upwardly opening cavity formed in the main foot part. Significantly, the ankle joint is positioned substantially further back, relative to the tip of the toes of the artificial foot, than heretofore attempted. The ball of foot part is mounted on a second pivotal axis and is in longitudinal alignment with the main foot part. Significantly, the ball of foot axis is positioned substantially further back, relative to the tip of the toes, than heretofore attempted. Each pivotal axis is transverse to the longitudinal axis of the artificial foot structure. The precise placement of the pivotal interconnection of the ball of foot part and the main foot part, the precise placement of the pivotal interconnection of the ankle part and said main foot part, as well as the spatial relation of the first and second pivotal axes to one another and to a support surface are all critical to the success of the invention. For example, if the first or second axis is placed forwardly or rearwardly of its novel position, a limping action will be created.

To better appreciate the substantial variance between the artificial foot of this invention and of the artificial feet heretofore known, the following percentages are provided, where the percentage given before the slash is the percentage distance of a first joint from the tip of the toes of an artificial foot and the percentage given after the slash is the percentage distance of a second joint from said tip of said toes of said artificial foot, where 100% represents the entire length of the artificial foot from the tip of its toes to the back of its heel:

| Roche | Foster | Haney | This Invention |
|---|---|---|---|
| 21%/66% | 30%/66% | 25%/75% | 35%/78% |

In other words, the Roche structure positions a toe joint 21% of the way from the tip of the toes to the back of the heel, and the ankle joint is 66% of said way. Haney positions the toe joint a little further back from the tip of the toes, and Foster positions said toe joint a little further back than Haney. However, all three of said prior art structures provide toe joints. In sharp and distinct contrast, the present invention positions the first joint back 35% from the tip of the toes, making said joint a joint in the ball of the foot region, not in the toe joint area. The present artificial foot is the first artificial foot having a joint in said ball of foot region of an artificial foot, said joint being 35% of the way from the tip of the toes to the back of the heel of said artificial foot. Just as importantly, both Roche and Foster position the ankle joint 66% of said way and Haney positions it 75% of said way. The present invention positions the ankle joint a full 78% of said way. Clearly, the 35%/78% positioning of the novel ball of foot and ankle joints fall outside the range heretofore known for artificial feet, and it is this important positioning of said ball of foot and ankle joints that provides the limp-free walk of this invention.

Preloaded compression springs are provided to resist pivotal motion between contiguous parts.

As recited in the claims that follow, the present invention is an artificial foot for an improved, more natural articulation and stride in walking use by a leg amputee. It includes a main foot part defining a heel of the artificial foot, an ankle part pivotally connected to an upper part of the main foot part for limited pivotal fore-and-aft movement about a first axis which is oriented generally transversely to a length of the artificial foot, and which first axis is positioned about 78% of the length of the artificial foot when measured from the tip of the toes to the back of the heel of the artificial foot. A ball of foot part is pivotally connected to the main foot part and is positioned about 35% of the length of the artificial foot when measured from the tip of the toes to the back of the heel.

The ankle part includes a substantially upright mounting post for connection with a lower end of an artificial leg, and front and rear substantially parallel, spaced resilient ankle compression members each preloaded in compression and positioned uprightly fore and aft, respectively, of the first axis. The front and rear compression members act between the main foot part and the ankle part so that the mounting post is maintained in a substantially upright at-rest orientation and is resiliently pivotable in either direction about the first axis first against the rear spring, and second against the front spring in walking use.

The ball of foot part is pivotally connected to a forward end of the main foot part for limited pivotal upward movement about a second axis that is generally parallel to the first axis. The second axis is closer to a ground-engaging surface of the artificial foot than the first axis.

A resilient ball of foot flexure compression member, preloaded in compression, is positioned and acts above the second axis between the main foot forward end and the ball of foot part so that the ball of foot part is held in an at-rest position against a stop means and is gradually pivoted upwardly about the second axis against the ball of foot flexure compression member during a later stage of each stride taken during walking use.

The second axis is positioned longitudinally with respect to the artificial foot at a distance about one-third of a length of the artificial foot from said forward end thereof (specifically, 35% as mentioned earlier) and about half way between the ground-engaging surface and the ball of foot flexure compression member. Moreover, the second axis is positioned vertically a distance of about one-quarter of a vertical distance of the first axis above the ground-engaging surface.

An inherent feature of the novel structure is that the structure automatically adjusts itself to changes in shoe heel heights. Thus, a wearer can adjust the novel foot to an ideal position suitable for the shoes the wearer most commonly wears, such as street shoes, and no shims are needed when the wearer switches to shoes having heel heights that differ from the heel heights of street shoes. This eliminates the bothersome use of shims required with prior art designs.

The novel foot structure is also energy-storing and energy-releasing.

It is a primary object of this invention to provide an artificial foot for a leg amputee which substantially duplicates the flexure, feel, stability and walking stride of a natural foot so that its wearer does not limp when walking or climbing stairs.

Another object is to provide an economical to manufacture artificial foot that may be suitably tailored in size, pivotal movement and resistive compression spring selection to accommodate the physical size and weight bearing needs of individual amputees.

A further object is to provide an artificial foot that is readily adaptable by prosthetic industry standards to the lower end of a leg prosthesis.

Another object is to provide an artificial foot that is self-adjusting to shoe heels of differing heights.

Yet another object is to provide an energy-storing foot.

Another major object is to disclose the precise locations that should be selected for a ball of foot joint and an ankle joint in an artificial foot.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
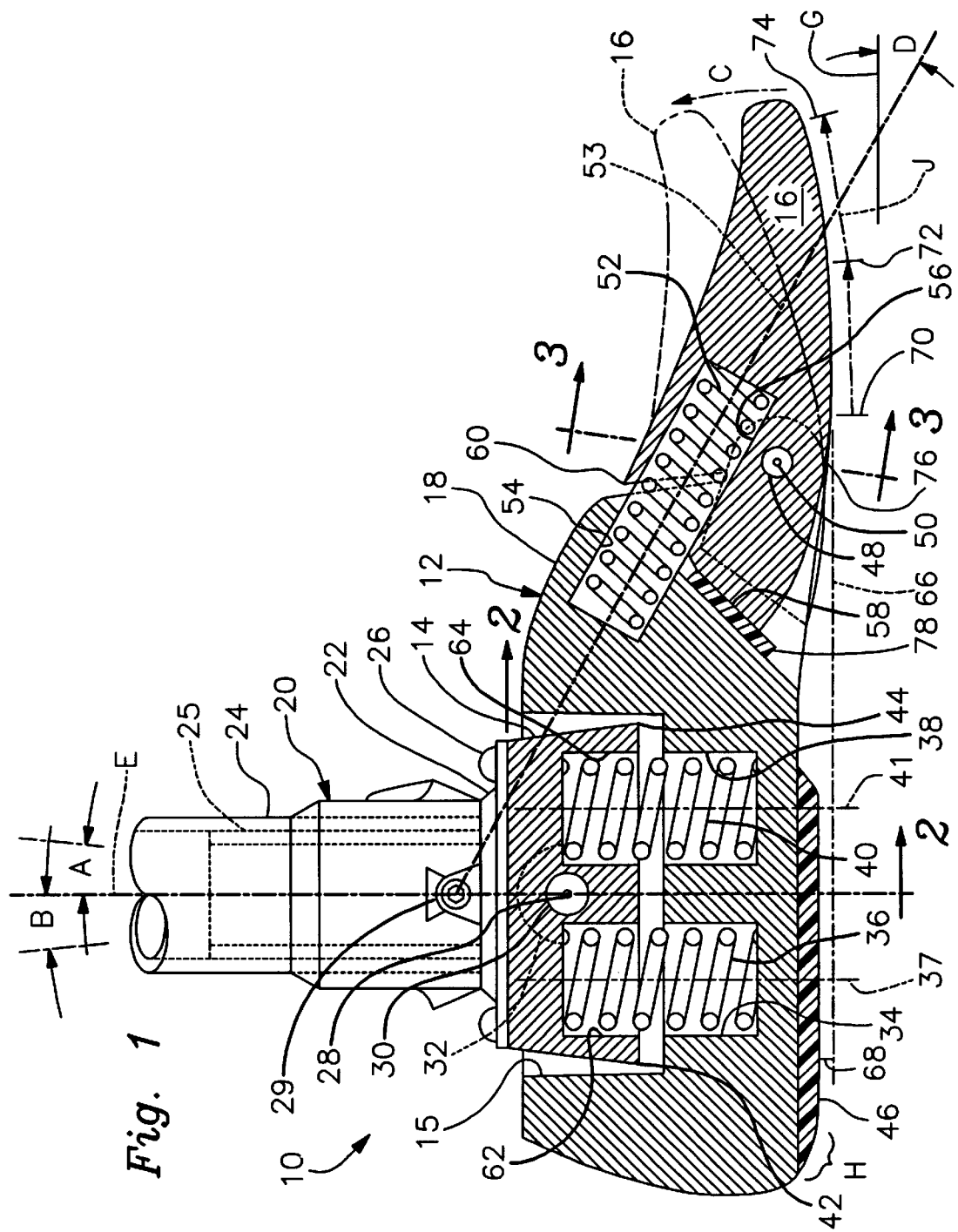
FIG. 1 is a side elevation, partial sectional view of an illustrative embodiment of the invention.

Referring now to FIG. 1, it will there be seen that an exemplary embodiment of the invention is denoted as a whole by the reference numeral 10; it includes an artificial foot assembly 12 and an industry standard fitting 20. The three primary components of assembly 12 are main foot part 18, ankle part 14, and ball of foot part 16. Each of these three main components are preferably formed of plastic or nylon and may be covered with a thin rubber covering material of suitable thickness to provide a natural external appearance. Components 14, 16, and 18 may be sized to fit into a conventional shoe or to be worn without a shoe, either exposed to view or covered at the option of the wearer.

Ankle part 14 is pivotally connected about transverse pivotal axis 28 by elongated ankle pin 30 that is positioned partially into an upwardly opening cavity 15 formed downwardly into main foot part 18. Axis 28 is in longitudinal alignment with a longitudinal axis of an artificial leg, not shown. If 100% represents the length of the artificial foot from the tip of its toes to the back of its heel, (i.e., the tip of the toes representing position 0% and the back of the heel representing position 100%), then axis 28 is positioned 78% of said total length as measured from said tip of said toes.

Figure 2:
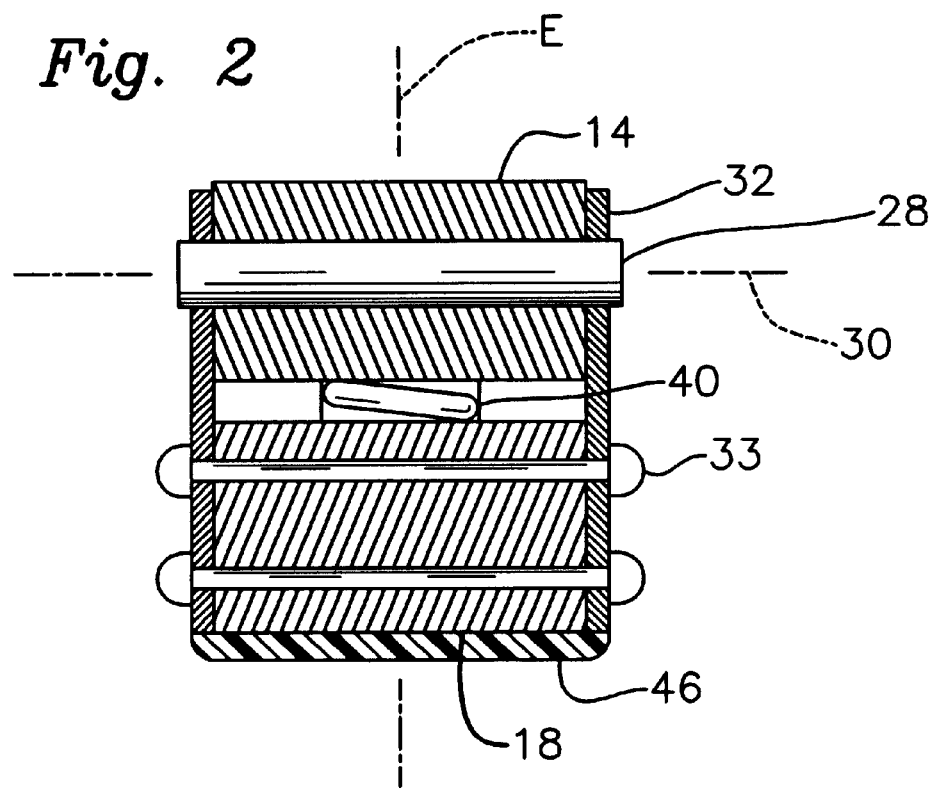
FIG. 2 is a sectional view taken along line 2—2 in FIG. 1.
Figure 3:
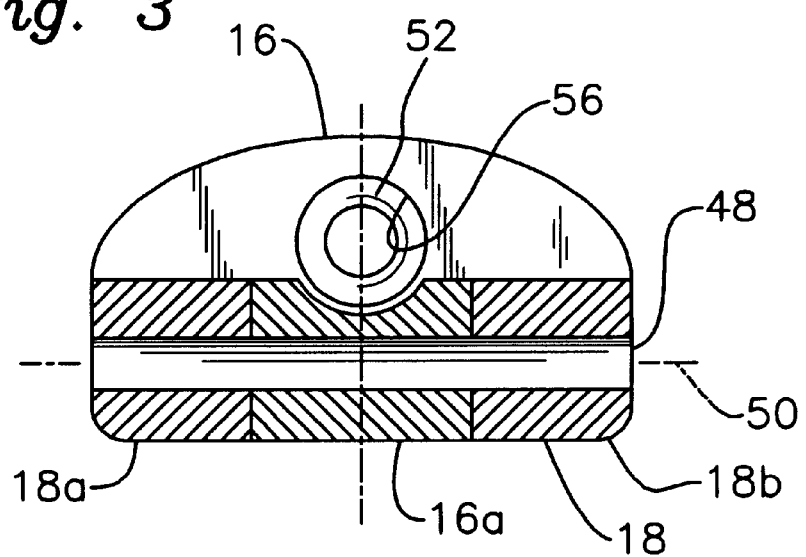
FIG. 3 is a sectional view taken along line 3—3 in FIG. 1.

As best depicted in FIG. 2, metal side plates 32 connected on either side of ankle part 14 and main foot part 18 may be provided for added strength in engaging ankle pin 30. Side plates 32 are rigidly connected by headed fasteners 33 to main foot part 18. When nylon and urethane parts are used in construction of the novel foot, braces 32 are not needed for persons of normal weight because such materials handle wear well; the braces may be needed, however, for persons of high weight.

Headed fasteners 26 rigidly connect industry standard fitting 20 atop ankle part 14 through a fixture mounting plate 22. Plate 22 includes a rigidly connected upwardly extending inner support tube 25 for mateable engagement within outer tube 24 for locking securement therebetween by set screw 29. Fixture 20 includes upwardly extending tube 24 for locking engagement into a lower end of an artificial leg (not shown).

Accordingly, ankle part 14 and fixture 20 are pivoted together about ankle pin 30 and first pivotal axis 28 fore and aft in the direction of arrows A and B, respectively. Such pivotal fore and aft movement is limited by contact of ankle part 14 at either 42 or 44 against a lower surface of cavity 15 of main foot part 18. Angle variation may be varied easily to meet individual needs.

Coil or compression springs 36 and 40 are positioned about upright parallel axes 37 and 41, respectively, within opposing pairs of cavities 62/34 and 64/38, respectively. These ankle springs 36 and 40 are preloaded in compression at assembly and always maintain a predetermined level of preloading as ankle part 14 is articulated fore and aft in the directions of said arrows A and B. Spring axes 37 and 41 are positioned evenly fore and aft on either side of axis E of ankle axis 28 and upright axis E of fixture 20.

Ball of foot part 16 is pivotally connected about a second transverse axis 50 by elongated ball of foot pin 48 which snugly passes through spaced parts 18a and 18b of main foot part 18 and a central rearwardly extending part 16a of ball of foot part 16. Pivotal movement between said two components is limited in extension by contact at 58 which defines the at-rest position of ball of foot part 16 and stop 60 which defines the upper limit of pivotal movement of the ball of foot part shown at 16 (in phantom) in the direction of arrow C about ball of foot axis 48.

The positioning of second pivotal axis 50 is critical to this invention because it is such positioning, together with the critical positioning of first axis 28, that eliminates the limp associated with earlier artificial foot designs. Transverse pivotal axis 50 is positioned longitudinally with respect to the device at about one-third the length of artificial foot 12 as measured from the forward end of the foot as a whole, i.e., from the tip of the toe. More particularly, defining the position of axis 50 in the same manner as the position of axis 28 is defined above, the position of axis 50 is at the 35% position. This places said axis in the ball of the foot region of the artificial foot, not at the toe joint as in earlier artificial feet.

The vertical positioning of said second pivotal axis 50 is also critical for the same reason; it is about half way between the ground-engaging surface of the foot and ball of foot spring 52. Another critical aspect of the present invention is the relative height positioning between first pivotal axis 28 and second pivotal axis 50. Specifically, first pivotal axis 28 is about four times higher than second pivotal axis 50, i.e., the height ratio therebetween is about 4:1. In other words, if second pivotal axis 50 is one unit of height above the ground surface, first pivotal axis 28 is about four of said height units above said ground surface.

Another compression spring 52 is positioned within mating cavity 54 of main foot part 18 at a first end thereof and within cavity 56 formed and extending into a rearwardly facing surface of ball of foot part 18. The preferred axis of orientation 53 of compression spring 52 is at a preselected angle D with respect to horizontal ground-engaging surface G. The preselected angle is about thirty degrees (30°), but a horizontal orientation is also acceptable. Compression spring 52 is installed with a compression preload to maintain the at-rest or in repose forwardly extending position of ball of foot part 16 as depicted in FIG. 1.

Rubber cushioned heel member 46 or a shoe heel (not shown) or any other suitable foot cover (not shown) makes the initial ground contact in region H during a normal walking step; this compresses rearward ankle spring 36. Angular movement in the direction of ankle B is limited by stop 42. As the stride continues, the weight of the individual shifts forwardly so that axis E passes through the in-repose position and moves forwardly in the direction of arrow A, compressing forward ankle spring 40. During this second part of the stride, the lower surface of ball of foot part 16 begins to support additional weight against ground G in the ball region of foot 12 to begin to pivot ball of foot part 16 in the direction of arrow C about ball of foot axis 50. This pivotal movement meets with increasing resistance upon further compression of ball of foot spring 52. Pivotal movement in the direction of arrow C is limited by stop 60. At the final stage of this part of the stride, all weight is lifted from the artificial foot and shifted to the other foot of the walker, whereupon ankle part 14 returns to the neutral, at-rest or in-repose position of axis E and ball of foot part 16 returns to its in-repose position against stop 58. It should therefore be clear that the novel artificial foot is an energy-storing foot. More particularly, as the various springs are compressed and released during a stride, said springs store and release energy, respectively.

It should be understood that the sizing and the strength of the various components, as well as the materials selection of each of the main components 12, 14 and 16, are adjustable by the prosthetist to accommodate the needs of individual patients.

Similarly, the strength of ankle springs 36 and 40 and ball of foot spring 52 are selectible within a reasonable range to accommodate the weight, size and stride of individual users. For example, a prototype includes ankle springs 36 and 40 having a one inch nominal outside diameter, a two inch length, a spring rate of about 1160 lbs. per inch and is preloaded in compression about 3/16". The ball of foot spring has a nominal outside diameter of 3/4" (but said diameter can range from 1¼" down to ½"), an overall free length of about 2", has a spring weight of about 400 lbs. per inch, and is preloaded in compression about 3/16". A broad selection of such springs, commonly known as die springs, are commercially available from multiple manufacturers such as Associated Spring/Raymond, Barnes Group, Inc., of Corry, Pa. Such springs may also be custom made. Fixture 20 is also commercially available from multiple sources, one of which is sold by Bock under the trademark Titan fixtures.

The positioning of ball of foot spring 52 is critical; it extends from a point near the ankle to a point in the ball of the foot. Its location is the same as the arch of a natural foot and it helps duplicate the action of the bones, tendons, muscles, tissue, etc. in the arch region of a natural foot.

Significantly, the action of ankle springs 36, 40 allows the novel foot to adjust to reasonable shoe heel height changes. The foot is first adjusted to accommodate the heel height of the wearer's regular shoes, in the in-repose position, and no shims are needed when shoes of differing heel heights are worn, i.e., the heel automatically adjusts to different heel heights.

The springs used in the novel foot may be of metallic or urethane construction; the latter is preferred because it is lighter in weight.

The critical absolute and relative positions of the first and second pivotal axes set forth hereinabove cooperate within one another to produce the first prosthetic foot that does not cause its user to limp. The critical respective locations of said first and second pivotal axes and the critical positioning of the ball of foot spring solves the limping problem completely. In view of the hundreds of years of development of the art of prosthetic feet that preceded this invention, it is obvious that the solution to the limping problem was not obvious to those of ordinary skill at the time this breakthrough invention was made. The art of prosthetic feet had become so petrified that it was thought by professionals in the field that the limping problem would never be completely overcome. This pioneering invention is the result of 1) rejecting the conventional wisdom that a limp-free foot prosthesis could never be developed and 2) engaging in prolonged creative thinking unrestrained and unhampered by the teachings and suggestions of earlier work in this field.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An artificial foot for an improved, more natural articulation and stride in walking use by a leg amputee, comprising:

a main foot part defining a heel of said artificial foot;

an ankle part pivotally connected to an upper part of said main foot part for limited pivotal fore-and-aft movement about a first axis which is oriented generally transversely to a length of said artificial foot, said ankle part including a substantially upright mounting post for connection with a lower end of an artificial leg;

front and rear substantially parallel, spaced resilient ankle compression members each preloaded in compression and positioned uprightly fore and aft, respectively, of said first axis and acting between said main foot part and said ankle part whereby said mounting post is maintained in a substantially upright at rest orientation and is resiliently pivotable in either direction about said first axis first against said rear spring, and second against said front spring in walking use;

a ball of foot part pivotally connected to a forward end of said main foot part for limited pivotal upward movement about a second axis that is generally parallel to said first axis, said second axis being closer to a ground-engaging surface of said artificial foot than said first axis;

a resilient ball of foot flexure compression member preloaded in compression and positioned in an area of said artificial foot that substantially corresponds to an arch area of a natural foot and acting above said second axis between said main foot forward end and said ball of foot part whereby said ball of foot part is held in an at-rest position against a stop means and is gradually pivoted upwardly about said second axis against said ball of foot flexure compression member during a later stage of each stride taken during walking use;

said second axis being positioned longitudinally with respect to said artificial foot at a distance about 35% of a length of said artificial foot from said forward end thereof where 100% represents a back of a heel position of said artificial foot and said second axis being positioned about half way between the ground-engaging surface and said ball of foot flexure compression member;

said second axis being positioned vertically a distance of about one-quarter of a vertical distance of said first axis above the ground-engaging surface; and said first axis being positioned about 78% of a length of said artificial foot from said forward end thereof where 100% represents a back of a heel position of said artificial foot.

2. An artificial foot for an improved, more natural articulation and stride in walking use by a leg amputee, comprising:

a main foot part defining a heel of said artificial foot;

an ankle part pivotally connected within an upwardly opening ankle cavity formed in an upper part of said main foot part for limited fore-and-aft pivotal movement about a first axis which is oriented generally transversely to a length of said artificial foot, said ankle part including an upwardly extending mounting post for connection with a lower end of an artificial leg;

a pair of substantially parallel, spaced ankle compression springs each preloaded in compression and positioned uprightly each spring being formed into a lower surface of said ankle part and said ankle cavity fore and aft, respectively, of said first axis and acting between said main foot part and said ankle part whereby said mounting post is maintained in a substantially upright at-rest orientation and is forcibly pivoted in either direction against one of said ankle spring at a time in walking use;

a ball of foot part connected to a forward end of said main foot part for limited pivotal movement about a second axis that is generally parallel to said first axis, said second axis being closer to, but above, a ground-engaging surface of said artificial foot than said first axis;

a ball of foot flexure compression spring preloaded in compression and positioned and acting above said second axis between said main foot forward end and said ball of foot part whereby said ball of foot part is held in an at-rest position against a stop means and is gradually pivoted upwardly about said second axis against said ball of foot flexure compression spring during each step taken with said artificial foot during walking use;

a first end of said ball of foot flexure compression spring seated in a mating cavity formed into said main foot forward end and a second end of said ball of foot compression spring seated in a mating cavity formed into a rearwardly facing surface of said ball of foot part;

said second axis being positioned vertically a distance of about one-quarter of a vertical distance of said first axis above the ground-engaging surface; and said first axis positioned 78% of the way from the forward end of said artificial foot and said second axis positioned 35% of said way where 100% represents the positioning of a back of a heel of said artificial foot.

* * * * *